United States Patent [19]

Karklin et al.

[11] 4,380,583

[45] Apr. 19, 1983

[54] METHOD OF PREPARING SEEDING MATERIAL FOR PRODUCTION OF CITRIC ACID

[76] Inventors: Roman Y. Karklin, ulitsa Veidenbauma, 45, kv. 13; Alma A. Rumba, ulitsa Putses, 12, kv. 3; Via K. Azanda, ulitsa Lenina, 237, kv. 1, all of Riga, U.S.S.R.

[21] Appl. No.: 252,040

[22] Filed: Apr. 8, 1981

[30] Foreign Application Priority Data

Apr. 19, 1980 [SU] U.S.S.R. ............................... 2932440

[51] Int. Cl.³ ............................................. C12N 3/00
[52] U.S. Cl. .................................... 435/242; 435/144; 435/254
[58] Field of Search ....................... 435/254, 144, 242

[56] References Cited

U.S. PATENT DOCUMENTS

| 3,000,791 | 9/1961 | Schweiger | 435/144 |
| 3,083,144 | 3/1963 | Shepard | 435/144 |
| 3,892,629 | 7/1975 | Smith et al. | 435/242 |

FOREIGN PATENT DOCUMENTS 568677  7/1977  U.S.S.R. .

Primary Examiner—R. B. Penland
Attorney, Agent, or Firm—Burgess, Ryan and Wayne

[57] ABSTRACT

Disclosed is a method of preparing a seeding material for the production of citric acid by cultivating spores of a fungus on a nutrient medium containing carbon and nitrogen sources and mineral salts and by separating spores from the nutrient medium.

The fungus used is the strain Aspergillus niger R-3 selected from the strain Aspergillus niger эү-119 by the stepwise action on it of ethyleneimine, N-nitrosomethylurea and ultraviolet radiation.

3 Claims, No Drawings

METHOD OF PREPARING SEEDING MATERIAL FOR PRODUCTION OF CITRIC ACID

FIELD OF THE INVENTION

The present invention is in the field of microbiological industries. More particularly it relates to a method of preparing a seeding material for citric acid production.

BACKGROUND OF THE INVENTION

There is known in the prior art (cf. R. Ya. Karklin, A. K. Probok. Biosynthesis of organic acids. Riga, 1972) a method of producing citric acid comprising the steps of preparing a seeding material of the strain *Aspergillus niger* эγ-119, fermentation under production conditions by cultivating spores (conidia) of said strain on a molasses-containing nutrient medium, and isolation of citric acid from the fermented broth. The strain *Aspergillus niger* эγ-119 (USSR Inventor's Certificate No. 170,898, published 11.05.1965) has the following morphological and cultural properties: A five-day-old culture grown on the Czapek-Dox broth has conidial heads round or starlike in shape, 85 to 190 mcm in diameter, double-layer sterigmata, with sterigma lengths being 11 mcm in the first order and 7.5 mcm in the second order, round conidia, 3.4 mcm in diameter, and conidiophores 0.7 to 0.5 mm long. A five-day-old gigantic colony grown on the Czapek-Dox broth is round, 40 mm in diameter; the substrate mycelium is radially pleated, the aerial mycelium is high, the conidia are dark brown, and the asporogenic zone is 7 mm. When grown on must agar, a five-day-old gigantic colony is round, fleecy, 73 mm in diameter, with an asporogenic zone of 11 mm. On a molasses medium, the strain *Aspergillus niger* эγ-119 provides a citric acid yield of between 70 to 75%, calculated with reference to the sugar content of the molasses used. On must agar, the yield of spores (conidia) per 1 $dm^2$ is 0.9 g. Conidia content is 15 to 20 billion per gramm.

The use of the strain *Aspergillus niger* эγ-119 in citric acid production gives a low spore yield at the stage of preparing the inoculum, with low biochemical activity characteristics.

Amongst the methods of preparing seeding materials for citric acid production to be found in literary sources, the closest to the item applied for herein is the method described in the USSR Inventor's Certificate No. 568,677 (published 15.08.1977). In this method, a seeding material of the strain *Aspergillus niger* R-1 is obtained by seeding a pure culture of the strain on a must agar nutrient medium of the following composition, in percent by mass:

| Sugar as beer must | 6 to 8 |
| --- | --- |
| Urea | 0.05 to 0.1 |
| NaCl | 1 to 2 |
| $CoSO_4$ | 0.0001 |
| Agar | 2 to 3 |

The pH of the medium is maintained at a level of 5 to 6.

Cultivation is carried out at a temperature of 30° to 32° C. for 9 to 10 days in cuvettes sized 10 to 12 $dM^2$. Ripe conidia are separated from the mycelium with the aid of a brush or a vacuum device. The yield of conidia per 1 $dm^2$ spore growth area is 1.0 to 1.1 g. Conidia content is 24 billion per gramm.

The strain *Aspergillus niger* R-1 has the following morphological and cultural properties: A five-day-old culture grown on the Czapek-Dox broth has conidial heads of round shape, 205 to 215 mcm in diameter, vesicles of oblong shape, 27 mcm in diameter, single-layer sterigmata, 10 mcm long, round conidia having a mean diameter of 7 mcm, and conidiophores 3 to 4 mm long and 20 mcm in diameter. A five-day-old gigantic colony grown on the Czapek-Dox broth is round, 45 to 50 mm in diameter; the colony margin is smooth, the asporogenic zone is 6 mm, the substrate mycelium is radially pleated, the sporophores are of medium density, the conidia are dark brown. When grown on must agar, a five-day-old gigantic colony is 90 mm in diameter, with sparse long sporophores in the centre of the colony, surrounded by a belt of abundant short sporophores which become sparse towards the margin.

On molasses media, with the superficial method of cultivation, the strain *Aspergillus niger* R-1 provides a citric acid yield of 99 to 100% based on the sugar content of the molasses used.

The strain *Aspergillus niger* R-1 as used in the production of citric acid is deficient in that it gives a low yield of spores (conidia) per unit spore growth area at the inoculum preparation stage and a low spore content per unit mass.

SUMMARY OF THE INVENTION

It is an object of the present invention to increase the yield of spores (conidia) per unit spore growth area and improve the quality of the seeding material (spore content per unit mass) in the production of citric acid, with the biochemical activity of the producer strain being at a high level.

Another object of the present invention is to reduce the costs involved in the production of citric acid.

These and other objects of the present invention are attained by the provision of a method of obtaining a seeding material for the production of citric acid, in which method spores (conidia) of the fungus *Aspergillus niger* are grown on a nutrient medium containing carbon and nitrogen sources and mineral salts and are separated from the nutrient medium, the fungus used, in accordance with the invention, being the strain *Aspergillus niger* R-3, selected from the strain *Aspergillus niger* эγ-119 by the stepwise action on it of ethyleneimine, N-nitrosomethylurea and ultra-violet radiation and having the following morphological and cultural properties: when grown on the Czapek-Dox broth, a five-day-old culture has rounded conidial heads, 200 to 220 mcm in diameter, single-layer sterigmata, with sterigma lengths of 9 to 15 mcm, vesicles of slightly oblong shape, sized 34×37 to 46×50 mcm, dark brown conidia, round in shape and 5 to 7 mcm in diameter, and conidiophores 1 to 3 mm long; a five-day-old gigantic colony grown on the Czapek-Dox broth is round, 40 to 45 mm in diameter, and has an asporogenic zone of 4 to 8 mm; when grown on must agar, a five-day-old colony is 46 to 48 mm in diameter, with a 6 to 10 mm asporogenic zone, has abundant sporophores and a convex-shaped centre with sparse dark-brown sporophores; the strain is highly resistant to antagonist bacteria that may occur in the process of citric acid fermentation; the citric acid yield is up to 100% with respect to the sugar content of the molasses used; no oxalic acid is formed in the process; on a must agar medium, the strain gives a yield of spores (conidia) of 1.3 to 1.45 g per 1 dm² of spore growth area, with a concentration of conidia of 30 to 35 billion per 1 grammm.

Said strain is deposited in the collection of the Central Museum of Industrial Microorganisms of the All-Union Genetics Research Institute. The strain number is TsMPMF 132.

The new strain *Aspergillus niger* R-3 has been isolated from the strain *Aspergillus niger* ₂γ-119 by the stepwise action of ethyleneimine, N-nitrosomethylurea and ultra-violet radiation.

The morphological properties of the new strain were studied on a culture grown on the Czapek-Dox broth, at a temperature of 32° C. The cultural properties of the strain were studied using the Czapek-Dox broth, must agar, and a composite spore cultivating medium citric acid. The biochemical characteristics of the strain were determined using a fermentation medium employed for preparing citric acid. Antagonistic properties were studied with reference to foreign microorganisms occurring in the process of citric acid fermentation.

The following properties are characteristics of the new strain:

1. Morphological properties

Czapek-Dox broth. A five-day-old culture has rounded conidial heads, 200 to 220 mcm in diameter, single-layer sterigmata, with sterigma lengths of 9 to 15 mcm, vesicles of slightly oblong shape, sized $34 \times 37$ to $46 \times 50$ mcm, dark-brown conidia, round in shape, 5 to 7 mcm in diameter, and 1 to 3 mm long conidiophores.

The morphological properties of the parent strain *Aspergillus niger* ₂γ-119, the strain *Aspergillus niger* R-1, and the new strain *Aspergillus niger* R-3 are compared in Table 1 below.

TABLE 1

| Characteristic | Unit | Strain -119 | Strain R-1 | Strain R-3 |
|---|---|---|---|---|
| Conidial head diameter | mcm | 105–115 | 205–215 | 200–220 |
| Vesicle size | mcm | $34 \times 35$ | $27 \times 30$ | $34 \times 37$ to $46 \times 50$ |
| Sterigma length | mcm | | | |
| first order | | | 11 | 10 | 9–15 |
| second order | | 7.5 | none | none |
| Conidium diameter | mcm | 3–4 | 7 | 5–7 |
| Conidiophore length | mm | 0.7–5 | 3–4 | 1–3 |

Cultural properties

Czapek-Dox broth. A gigantic colony grown in a Petri dish at a temperature of 32° C. for five days is round in shape and 40 to 45 mm in diameter. The spores are sparse, the conidiophores are low, the conidial heads are small in size and dark brown in colour. The asporogenic zone is 4 to 8 mm.

Must agar. Five-day-old gigantic colonies are round in shape and 46 to 48 mm in diameter. The sporophores are low, dense and dark brown in colour, with sparse sporophores in a convex-shaped colony centre. The asporogenic zone is 6 to 10 mm.

A spore cultivating medium composed, in percent by mass, of sugar as beer must (7), urea (0.05), sodium chloride (2), copper sulphate (0.0001), agar (2.4), the balance being water. A white slightly pleated mycelium develops during the first two days. On the third day, there are abundant short sporophores, with large-sized conidial heads of dark-brown to black colour. The spore yield is 1.3 to 1.45 g per 1 dm² of spore growth area. The spore content is 30 to 35 billion per gramm.

Behaviour toward carbon sources

The proposed strain assimilates saccharose, glucose, fructose, maltose, hydrolyzates of vegetable matter, ethanol. Will not assimilate acetic acid.

Behaviour toward nitrogen sources

The proposed strain assimilates nitrogen of organic or mineral origin.

Antagonistic properties

The proposed strain is resistant to gas-, acid-, and nitrite-forming bacteria such as occur in the fermentation process of the citric acid production.

Biochemical properties

The proposed strain digests well molasses solutions to give a citric acid yield of up to 100% based on the sugar content of the molasses used. Citric acid accounts for 95 to 99% of the total of the acids synthesized.

The biochemical properties of the strains *Aspergillus niger* ₂γ-119, R-1 and R-3 are compared in Table 2.

TABLE 2

| *Aspergillus niger* strains | Citric acid yield, percent of molasses sugar | Spore yield per 1 dm² of spore growth area | Spore content per gramm, bill. |
|---|---|---|---|
| -119 | 70–75 | 0.9 | 15–20 |
| R-1 | up to 100 | 1.0–1.1 | 20–24 |
| R-3 | up to 100 | 1.3–1.45 | 30–35 |

The proposed method of obtaining a seeding material for the production of citric acid can be implemented as follows:

First, a nutrient medium is prepared, containing carbon and nitrogen sources and mineral salts. Beer must or malt extract containing 5 to 9 percent by mass of sugar are normally used as carbon sources. The nitrogen sources generally used are urea, ammonium nitrate, or ammonium chloride.

The nutrient medium may have the following composition, in percent by mass:

| | |
|---|---|
| sugar as beer must or malt extract | 5–9 |
| urea | 0–0.2 |
| NaCl | 0–3 |
| CuSO$_4$.5H$_2$O | 1.8–3 |
| water | balance |

The nutrient medium is prepared in a heated vessel fitted with a stirring device. Agar is soaked first, as a preliminary step, to be then melted during 20 to 30 minutes while being stirred and gradually heated to 80° C. Beer must or malt extract is added, with stirring, to the molten agar. Sodium chloride, copper sulphate and urea are dissolved in water, with stirring, and added into the vessel. The contents of the vessel are stirred, and water is added to make up the required volume.

The nutrient medium thus prepared is dispensed into cuvettes, covered over by cotton-wool-and-gauze blankets, and placed into an autoclave to sterilize at a temperature of 120° C. for 20 to 30 minutes. The sterilized cuvettes are transferred into a heating chamber.

The solidified nutrient medium is innoculated with spores of the source culture *Aspergillus niger* R-3. The spores may be used as such, or they may be mixed with an extender (activated carbon, talc or chalk) in a ratio of between 1:1 to 1:10. A spray gun type device is used to perform the inoculation. Another way to inoculate the nutrient medium is to use spores in the form of a slurry. The amount of spores used for inoculation is 1 to 2 mg per 1 dm$^2$ of the nutrient surface area.

Cultivation of the spores in the heating chamber takes 8 to 10 days.

The process of cultivation is carried out under temperature and humidity conditions being either controlled or constant.

Air humidity in the heating chamber is controlled using a humidifier and sterile air aeration to bring down the relative humidity gradually from 90 to 40 percent. The temperature is controlled to be gradually decreased from 33°-34° C. to 20°-25° C. Spores are collected from the surface of the mycelium into a vessel under sterile conditions, using a brush or a vacuum device.

The collected seeding material is weighed. 1 dm$^2$ of the spore growth area yields 1.3 to 1.45 g of spores. The number of spores is determined in a counting chamber. 1 gramm contains 30 to 35 billion spores. Spores are mixed with an extender (activated carbon, talc, or chalk) in a ratio of 1:1 to 1:2.

The ready-for-use seeding material is analyzed for biochemical activity and germinating capacity.

Acid formation activity is determined under laboratory conditions by cultivating sporea on molasses-containing fermentation media (sugar content 13 to 15 percent) such as are used in the production of citric acid.

Cultivation is performed by the superficial method in an 8 to 12 cm thick layer, at a temperature of 30° to 32° C. and pH equal to 6.7 to 7.0 for 7 to 8 days. The fermented molasses solution is titrated with caustic soda to determine the yield fo synthesized acids. The concentration of citric acid is determined by the calcium salts method, spectrophotometry, or iodometry. Citric acid accounts for 95 to 99 percent of the total of the acids synthesized. The citric acid yield as referred to the sugar content of the molasses used is 95 to 100 percent. The oxalic acid concentration referred to the total of the acids synthesized is zero to 1 percent.

The spore germinating capacity is determined on a microscope slide in a suspended drop of a molasses or must solution. The germinating capacity of spores is 95 to 98 percent.

The relevant characteristics of the strains *Aspergillus niger* эγ-119, R-1, and R-3 are compared in Table 3:

TABLE 3

| *Aspergillus niger* strains | Citric acid yield, percent of molasses sugar | Spore yield per 1 dm$^2$ of spore growth area, g | Spore content per gramm, bill. |
|---|---|---|---|
| -119 | 70-75 | 0.9 | 15-20 |
| R-1 | up to 100 | 1.0-1.1 | 20-24 |
| R-3 | up to 100 | 1.3-1.45 | 30-35 |

The seeding material is to be stored at a relative air humidity not exceeding 70 percent. Storage temperature is 20° to 25° C. The storage life of the spores is 6 months from the date of production.

The following typical examples will further illustrate the present invention in certain aspects, bringing forth more clearly the features and advantages specific to it.

EXAMPLE 1

The strain *Aspergillus niger* R-3 was used to prepare the seeding material.

The nutrient medium has the following composition in percent by mass:

| | |
|---|---|
| sugar as beer must | 7 |
| urea | 0.05 |
| NaCl | 2 |
| CuSO$_4$.5H$_2$O | 0.0001 |
| agar | 2.4 |
| water | balance |

The nutrient medium was prepared in a digester (500 l) fitted with a powered stirrer and heated with steam. 11.76 kg of agar was soaked in 220 l of water and held at normal temperature for 24 hours. Then the stirrer was started up, and the contents of the digester was slowly heated up, with stirring, to 80° C. during 20 to 30 minutes. 214 l of beer must (sugar content 16 percent) was then added to and stirred with the molten agar. Next 9.8 kg of NaCl, 0.254 kg of urea and 0.49 g of CuSO$_4$.5H$_2$O were dissolved in 10 l of water, and the solution obtained was charged into the digester. The contents of the digester was stirred, and water added to bring the volume to 490 l.

The nutrient medium so obtained was dispensed through a metering device into cuvettes (totalling 350). Each cuvette had a surface area of 11 dm$^2$. Covered over with cottom-wool-and-gauze blankets, the filled cuvettes were sterilized in an autoclave at a temperature of 120° C. for 30 minutes.

The sterilized cuvettes were placed into a heating chamber. The solidified nutrient medium was innoculated with spores of the strain *Aspergillus niger* R-3 mixed with activated carbon in the ratio of 1:1. A spray gun type device was used to perform the inoculation. The amount of spores used for inoculation was 1 mg per 1 dm$^2$ of the nutrient surface area.

The process of spore cultivation was carried out for 9.5 days under controlled temperature and humidity conditions. In the course of the first 4 days of development of the fungus the air humidity in the heating chamber was gradually lowered from 80 to 60 percent, and in the next 4.5 days, from 60 to 40 percent. A humidifier and aeration with sterile air were used for the purpose. The temperature was controlled automatically: 32±1° C. was maintained during the first 4 days, 30±1° C. during the next 4.5 days, and 20°-25° C. during the last day.

Spores were collected from the surface of the mycelium by means of a vacuum device into 2 aluminium flasks measuring 20 l each and then weighed. 5582 g of spores were collected from 3850 dm$^2$ of spore growth area, which comes to 1.45 g per 1 dm$^2$. The number of spores was determined in a counting chamber, the result being 35 billion spores per 1 gramm. Activated carbon in the amount of 5582 g was added to and thoroughly mixed with the collected spores.

The ready-for-use seeding material was analyzed for biochemical activity and germinating capacity.

The biochemical activity of the seeding material was determined by titrating with NaOH a fermented molasses solution. The citric acid yield was found to be 99 percent of the sugar content of the molasses used. There was no evidence of oxalic acid.

The germinating capacity of the spores was determined on a microscope slide in a suspended drop of a molasses solution.

The germinating capacity was found to be 98 percent.

EXAMPLE 2

The procedures used for preparing the nutrient medium and innoculated it with spores of the strain *Aspergillus niger* R-3 were essentially as described in Example 1.

Cultivation of spores was performed in a heating chamber at a constant temperature of 31±1° C. for 8 days. Humidity was not controlled. The last day the cuvettes were maintained at a temperature of 20° to 25° C. The spores were collected to prepare the seeding material as described in Example 1. 1.35 g of spores was collected from 1 $dm^2$ of the spore growth area, the total area yielding 5197.5 g.

The number of spores per 1 gramm was 30 billion.

The biochemical activity of the spores was determined as 96.4 percent of citric acid based on the sugar content of the molasses used.

The germinating capacity of the spores was 97.5 percent.

EXAMPLE 3

Cultivation of the spores *Aspergillus niger* R-3 was carried out on a nutrient medium having the following composition in percent by mass:

| | |
|---|---|
| sugar as malt extract | 8 |
| urea | 0.1 |
| NaCl | 1 |
| $CuSO_4.5H_2O$ | 0.0001 |
| agar | 2 |
| water | balance |

The nutrient medium was prepared in the volume and using the procedure described in Example 1.

Temperature and humidity were controlled as described in Example 1.

5005 g of spores were collected from 3850 $dm^2$ of spore growth area, which gives 1.30 g per 1 $dm^2$.

The biochemical activity of the seeding material was determined as 95.2 percent of citric acid based on the sugar content of the molasses used.

The germinating capacity of the spores was 97 percent.

The proposed method of preparing a seeding material is of particular importance where a large-scale production of citric acid is involved—when it pays to set up a special operation for the production of seeding material which could be stored for long periods under normal conditions and transported over long distances.

The proposed method enables a high yield of spores, exceeding the present-day level by as much as 30 percent.

The quality of the seeding material afforded by the proposed method assures a high yield of citric acid, amounting to as high as 100 percent of the sugar content of the molasses used.

We claim:

1. A method of preparing a seeding material for the production of citric acid comprising cultivating the fungus *Aspergillus niger* R-3 strain TsMPMF 132 on a nutrient medium containing a carbon source selected from the group consisting of malt extract and beer must, a nitrogen source, and at least one mineral salt to form spores and separating said spores in an amount in excess of 1.3 g/dm from the nutrient medium.

2. The method of claim 1 further comprising conducting the cultivating step at a temperature between 20° and 34° C.

3. The method of claim 1 or 2 wherein said nitrogen source is selected from urea, ammonium nitrate and ammonium chloride.

* * * * *